(12) United States Patent  (10) Patent No.: US 9,194,775 B2
Schiffenbauer  (45) Date of Patent: Nov. 24, 2015

(54) GUIDED SLICING SYSTEM FOR OBTAINING HISTOLOGICAL SAMPLES AND METHODS THEREOF

(71) Applicant: ASPECT IMAGING LTD, Shoham (IL)

(72) Inventor: Yael S. Schiffenbauer, Kidron (IL)

(73) Assignee: ASPECT IMAGING LTD., Shoham (IL)

( * ) Notice: Subject to any disclaimer, the term of this patent is extended or adjusted under 35 U.S.C. 154(b) by 265 days.

(21) Appl. No.: 13/954,235

(22) Filed: Jul. 30, 2013

(65) Prior Publication Data
US 2014/0030757 A1  Jan. 30, 2014

Related U.S. Application Data

(60) Provisional application No. 61/677,012, filed on Jul. 30, 2012.

(51) Int. Cl.
G01N 1/28 (2006.01)
G01N 1/06 (2006.01)
G01N 1/31 (2006.01)

(52) U.S. Cl.
CPC ............... G01N 1/286 (2013.01); G01N 1/06 (2013.01); G01N 1/312 (2013.01)

(58) Field of Classification Search
None
See application file for complete search history.

(56) References Cited

U.S. PATENT DOCUMENTS

| 8,189,737 | B2 | 5/2012 | Keller et al. |
| 2002/0010394 | A1 | 1/2002 | Zavislan |
| 2007/0091428 | A1* | 4/2007 | Wilson et al. ............... 359/391 |
| 2008/0260217 | A1* | 10/2008 | Mashiach ............... 382/128 |

OTHER PUBLICATIONS

Office Action dated Jan. 27, 2014 by SIPO in corresponding Chinese Application No. 201320624356.3.
Rapoport, Preclinical Imaging: The use of preclinical magnetic resonance imaging (MRI) for characterization of disease progression and response to therapy, retrieved from <<http://www.webworldarticles.com/e/a/title/Preclinical-Imaging:-The-use-of-preclinical-MRI-for-characterization-of-disease-progression-and-response-to-therapy/>> on Jul. 30, 2013.
Madabhushi et al., Automated Detection of Prostatic Adenocarcinoma From High-Resolution Ex Vivo MRI, IEEE Transactions on Medical Imaging, Dec. 2005, pp. 1611-1625, vol. 24, Issue 12, IEEE.
Alic et al., Facilitating Tumor Functional Assessment by Spatially Relating 3D Tumor Histology and In Vivo MRI: Image Registration Approach, PLoS ONE Journal, Aug. 2011, pp. 1-10, vol. 6, Issue 8, Public Library of Science.
McGrath et al., Fiducial Markers for Correlation of Whole-Specimen Histopathology with MR Imaging at 7 Tesla, Med. Phys., May 2010, pp. 2321-2328, vol. 37, Issue 5, Toronto, Canada.

* cited by examiner

Primary Examiner — Bhavesh Mehta
Assistant Examiner — Amandeep Saini

(57) ABSTRACT

Systems and methods for providing guided slicing of histological samples. The samples are acquired, spacially labeled with a fiducial marker, and imaged with a scanning system. The images are analyzed, either manually, semi-automatically or automatically, and likely locations of pathologies are identified. A slicing program is then generated and the sample sliced according to the slicing program, thereby ensuring that likely locations of pathologies are analyzed.

18 Claims, No Drawings

GUIDED SLICING SYSTEM FOR OBTAINING HISTOLOGICAL SAMPLES AND METHODS THEREOF

FIELD OF THE INVENTION

The present invention pertains to a computer assisted diagnosis (CAD)-based or a manual guided-slicing system for obtaining histological samples and to guided-slicing methods thereof.

BACKGROUND OF THE INVENTION

In the diagnosis and treatment of cancer and other diseases, as well in the development of new drugs and medical therapeutic procedures, it is often necessary to take a biopsy to determine if the mass is malignant or benign. Pathological examination of a lesion in the body tissue of an animal which has a natural or surgically exposed surface, usually requires that a pathologist interpret slides prepared from sections of the tissue specimen or lesion, i.e., histologically prepared sections or slices.

Preclinical evaluation of new drugs and medical care, for example in toxicology studies for a drug under development, or a material under investigation, routinely involve excision, fixation and slicing of target organs for pathology assessment. These organs, e.g., liver, heart, kidneys, gut, brain of laboratory animals, such as mice and rats are examined by histology to identify various pathologies, such as tumors, ischemic lesions, deformations, inflammation, hyperplasia, fibrosis, etc. In the course of each preclinical trial, a dozen, and hundreds, even thousands of organs are examined.

As is underlined in Zaviskan, US patent application 20020010394, borders of the slices are referred to as margins and may contain diseased or healthy tissue. After suitable processing, the tissue specimen or slices thereof are embedded or otherwise fixated e.g., in paraffin blocks or by frizzing unfixed specimens. Histological sections are then cut from the tissue slices with a microtome and stained for microscopic examination and interpretation by a pathologist. It is generally required that the histologically prepared sections from the tissue specimen represent a common suite or set of sections selected to provide information to diagnose the type of pathologic lesion and its extent. This suite of sections may generally include at least one section along the major axis of the tissue ellipse (i.e., along the length of the ellipse), at least one to two sections on each side of the tissue ellipse transversing the major axis, and at least three to four sections from the center of the lesion. The number of slices in the suite increases with the size of the lesion, its condition before and after cutting, embedding and processing.

A WEB article "Preclinical imaging: The use of preclinical magnetic resonance imaging (MRI) for characterization of disease progression and response to therapy" indicates that MRI is been widely used in preclinical research on experimental small animals. Studies have typically been aimed at understanding the pathophysiological status and evaluating the efficacy and side effects of newly developed treatments such as pharmaceutical and regenerative medicine.

When having in hand the target organ to be sliced for pathological investigation, there are conventions and technical procedures on how many slices to obtain from the organ. In an organ of a few centimeters, when slicing a few slices of approximately 5 µm each, the lesion, even if present, can be missed. Image analysis techniques are utilized in the domain of histopathology, specifically for the objective of automated carcinoma detection and classification. CAD systems have been implemented to aid histopathologists and clinicians in cancer diagnosis and research, which have been attempted in order to significantly reduce the labor and subjectivity of traditional manual intervention with histology images. Hence, for example, Madabhushi et al., Automated Detection of Prostatic Adenocarcinoma From High-Resolution Ex Vivo MRI IEEE Transactions On Medical Imaging, Vol. 24, No. 12, December 2005 discloses an automated computer-aided detection (CAD) system for detecting prostatic adenocarcinoma from 4 Tesla ex vivo magnetic resonance (MR) imagery of the prostate. Madabhushi's CAD system was thus designed for enhancing visual detection of prostate cancer, and thus to overcome lack of shape, differences in texture and image intensity, and to avoid image overlapping between malignant and benign structures. Madabhushi's method for improved imageability was as follows: (a) acquiring [MR] images of the adenocarcinoma; (b) correcting for background inhomogeneity and nonstandardness; (c) extracting three-dimensional (3-D) texture features from the 3-D MRI scene; (d) assigning, by means of a Bayesian classifier, each image voxel a "likelihood" of malignancy for each feature independently; (e) combining said "likelihood" images using an optimally weighted feature combination scheme; (f) quantitatively evaluating by comparing the CAD results with the manually ascertained ground truth for the tumor on the MRI; and then (g) visually registering the MR slices with the corresponding regions on the histology slices thereby manually determining tumor labels on the MR slices by an expert.

Alic et al., see: Facilitating Tumor Functional Assessment by Spatially Relating 3D Tumor Histology and In Vivo MRI: Image Registration Approach. PLoS ONE 6(8): e22835. doi:10.1371/journal.pone.0022835; 2011, shows that established 3D correspondence between tumor histology and in vivo MRI enables extraction of MRI characteristics for histologically confirmed regions. The proposed methodology allows the creation of a tumor database of spatially registered multi-spectral MR images and multi-stained 3D histology.

McGrath et al., in Fiducial Markers for Correlation of Whole-Specimen Histopathology with MR Imaging at 7 Tesla. Med Phys. 2010 May; 37(5):2321-8, shows registration of 3D histopathology with 3D in vivo imaging validated tumor boundary delineation for targeted radiation cancer therapy. They have also shown that accurate correlation is compromised by tissue distortion induced by histopathological processing.

U.S. Pat. No. 8,189,737 discloses a processes for producing a microCT image for virtual histology using x-ray microscopic computed tomography along with processes for rapid and inexpensive high-throughput methods of high resolution imaging for screening an ex vivo embryo for phenotype using computed tomography imaging.

It is thus a long felt need to obtain either a CAD-based or manually guided slicing system for obtaining histological specimens and guided slicing methods; decreasing the chance of misdiagnosis due to missing the right slice in the sample and increasing by that the "likelihood" of detecting malignancy or any other pathology.

DETAILED DESCRIPTION OF THE PREFERRED EMBODIMENTS

The term 'fiducial marker' refers hereinafter to either a virtual computer-generated or physical object used in the field of view of an imaging system which appears in the image produced, for use as a point of reference or a measure. It may be either something placed into or onto the imaging subject, or a mark or set of marks in the reticle of an optical instrument.

The term 'sample' refers hereinafter in a non-limiting manner to one more members of a group consisting of organs, tissues, cells, culture, culture of organ tissues, the whole sample (e.g., brain, heart, kidney, placenta, prostate, spleen, spinal cord, trachea, testis, uterus, fetal brain, fetal liver, adrenal gland, liver, lung, small intestine, spleen, salivary gland, skeletal muscle, thymus, trachea, thyroid, spinal cord, breast, colon, ovary, stomach, etc.) and any portion thereof, excisions thereof, specimens thereof, cuts thereof, slices thereof, biopsies thereof, processed biopsies, embedded biopsies, fixed biopsies, extracts thereof, and otherwise processed any material thereof; of any organism, especially organisms selected from a group consisting of animals, (e.g., laboratory animal, farm animals, etc) and humans.

The term 'about' refers hereinafter to a value being ±25% of the defined measure. It is one object of the invention to disclose a first method of guided-slicing of histological specimens. This method comprises, inter alia, steps as follows: (a) excision extracting a sample from a human patient, a laboratory animal or any other biological source, e.g., in vivo, ex vivo or in vitro origin, by any procedure known in the art; (b) two dimensional [2D] or three dimensional [3D] (i.e., spatially-) labeling the sample by a fiducial marker; (c) acquiring ex vivo images of the sample in spatial orientation (hereinafter 'coordination') with the fiducial marker; virtually slicing said image, thereby defining, according to the fiducially marked images N computer-retrievable 2D or 3D image slices (hereinafter '3DISs'). N is an integer greater than or equal to 2; and (d) physically slicing said image, wherein the steps of physically slicing the sample are preceded by steps of preparing, from the N 3DISs, at least one of a (i) man made manual and/or (ii) CAD-based slicing program of suspected computer-retrievable three-dimensional image slices (SISs); positions of the physical slices of the sample being provided by physically slicing the sample along the SIS lines or planes thereof (hereinafter 'slicing SIS').

This method comprises, inter alia, steps as follows: (a) spatial labeling of the sample by a fiducial marker; (b) acquiring ex vivo, by at least one first imaging device, one or more images of the sample in spatial coordination with the fiducial marker; and defining N computer-retrievable two-dimensional or three-dimensional image slices [3DISs], N is an integer greater than or equal to 2; (c) assigning, by at least one second imaging device, "likelihood" of malignancy or pathology of any kind for each of the N 3DISs; (d) defining, from the N SDISs, M suspected computer-retrievable three-dimensional image slices [SISs], M is an integer greater than or equal to 0; and (e) preparing a (i) manual and/or (ii) CAD-based slicing program. The physical slicing of the extracted and pre-analyzed biopsy is provided by slicing the sample according to the SISs.

It is another embodiment of the invention to disclose the method as defined in any of the above, wherein the aforesaid steps of spatially labeling the sample are provided by placing the fiducial marker (i) into and/or (ii) onto the surface of the sample.

It is another embodiment of the invention to disclose the method as defined in any of the above, wherein the aforesaid step of spatially labeling the sample is provided by one or more of the following: physically incorporating a physical imageable member and/or radiation emitting/absorbing agents; introducing biological active agents, such as enzymes, proteins and antigens/antibodies; interacting one or more chemical materials and compositions thereof, such as reactants and the like; and/or by a computer-generated fiducial marker.

It is another embodiment of the invention to disclose the method as defined in any of the above, wherein the aforesaid step of acquiring an image is provided by one or more members of a group consisting of CT, computer-assisted tomography; IR, rendered images comprising infrared light (spectroscopy; MRI, magnetic resonance imaging, PET, positron emission tomography; fluorescence and phosphorescence microscopy, ultrasound and the like.

It is another embodiment of the invention to disclose the method as defined in any of the above, wherein the aforesaid steps of preparing the slicing program of suspected computer-retrievable three-dimensional image slices (SISs) comprises one or more steps of defining from the N 3DISs a number I of first SISs and J second SISs. The slicing-plane of the I first SISs and the slicing-plane of the J second SISs are oriented in a non-parallel manner, forming at least one intersection angle $\phi$. Intersection angle $\phi$ can be smaller than about 170 degrees or greater than about 190 degrees. The line of intersection is either straight or curved. I and J are integers, each of which is greater than or equal to 1.

It is another embodiment of the invention to disclose the method as defined in any of the above, wherein the aforesaid step (d) of slicing is provided by any of the slicing, splitting, fractionalizing, layering, sectioning or cutting devices known in the art, e.g., microtome, vibrotome or their like.

It is another object of the invention to disclose a second method of CAD-based or manual guided-slicing of histological samples. This method may further incorporate a first imaging of a pre-sliced spatially oriented sample for indicating malignancy or any other pathology "likelihood" and a second imaging for re-slicing those slices that are more likely to be malignant/pathological slices.

Another object of the present invention is to disclose a first guided slicing system for obtaining histological slides. This system is arranged and constructed as one of the following: a fully automated system, a partially automated system and a non-automated, manually-activated system. This is either CAD-based or manual system which comprises, inter alia, modules as follows: a sample kit for extracting a sample; a fiducial marker for spatially labeling the sample; an imaging device for acquiring one or more ex vivo images of either a pre-extracted or post-extracted sample in spatial-orientation and 2D or 3D coordination with the fiducial marker; a processor for virtually slicing the imaged sample into N computer-retrievable two-dimensional or three-dimensional image slices [3DISs], N is an integer greater than or equal to 2; and for preparing a (i) manual and/or (ii) CAD-based slicing program; and either a microtome or a vibrotome for slicing the sample according to the aforesaid SIS.

Another object of the present invention is to disclose a second guided slicing system for histological specimens. This system is also arranged and constructed as one of the following: a fully automated system, a partially automated system and a non-automated, manually-activated system. Similarly, this system is provided either as CAD-based or manual system which comprises, inter alia, modules as follows: means for extracting a sample; a fiducial marker for spatially labeling the extracted sample; at least one first imaging device, for acquiring ex vivo one or more images of the sample in spatial coordination with the fiducial marker; at least one second imaging device, for assessing the "likelihood" of malignancy or any other kind of pathology for each of the N 3DISs; a processor for (i) virtually slicing the sample into N computer-retrievable three-dimensional image slices [3DISs], N is an integer greater than or equal to 2; (ii) defining from the N 3DISs, M suspected computer-retrievable three-dimensional image slices [SISs], M is an integer greater than or equal to 0; and, (iii) preparing a manual and/or CAD-based slicing program based on the SISs; and a slicing machine for slicing the sample according to the aforesaid SISs.

It is another embodiment of the invention to disclose the system as defined in any of the above, wherein the imageable fiducial marker is selected from one or more member of a group consisting of the aforesaid physical members, biological agents, chemical materials and virtual computer-generated markers.

It is another embodiment of the invention to disclose the system as defined in any of the above, wherein the aforesaid first imaging device, second imaging device or both are selected from a group consisting of: X-ray computed tomography (CT), MRI, positron emission tomography (PET), fluorescence and phosphorescence microscopy (FPM), and ultrasound (US), rendered images comprising infrared light (IR) spectroscopy and the like and any combination thereof.

It is another embodiment of the invention to disclose the system as defined in any of the above, wherein the processor prepares the slicing program of suspected computer-retrievable three-dimensional image slices (SISs) in a method comprising steps of defining, from the N 3DISs, a number I of first SISs and J second SISs; wherein the slicing plane of the I first SISs and the slicing plane of the J second SISs are oriented in an non-parallel manner; and further wherein I and J are integers greater than or equal to 1.

It is thus in the scope of the invention wherein a pre-clinical study is performed to test the adverse effects of a new compound, such as a drug under development, a new food additive and a new herb extract. Animals, such as mice and rats, are exposed to a predefined measure of the new compound for a predefined period of time under predefined conditions. During and/or after the period of time, a variety of tests is performed, such as weighing the animal, urine and blood tests, etc. Then a variety of organs, such as the liver, kidney, heart, lungs, brain, intestines, or ovaries are extracted for histological examination. MRI is performed on the ex vivo organs BEFORE slicing them to make the histological slides. The MRI should aid slicing in the right place.

The specimens are fixed and sent to histology where they are sliced according to specific guidelines and a predefined number of slices (5 mm) are chosen, from which histology slides are prepared. The preparation includes, inter alia and in a non-limiting manner, coating the sample with paraffin etc. Before further preparation, an MRI-image of the specimen is taken, and a specific reference marker, such as fiducial marker is used, and a CAD-guided slicing program, as described hereinabove, is generated. Preparation then continues, comprising slicing in a microtome based on the CAD-guided slicing program, placing some of the slices on a microscopy slide, staining of the slices and then analyzing them using a light microscope. Thus the CAD-guided slicing is provided in optimal locations where there is indication of some kind of pathology: tumor, inflammation, holes, disrupted tissue, blockage, necrosis etc., and not just arbitrarily, where blind slicing may miss the pathological portion.

The invention claimed is:

1. A method of guided slicing for obtaining histological specimens, comprising steps of:
   a. extracting a sample from an animal;
   b. spatially labeling said sample by a fiducial marker;
   c. acquiring ex vivo images of said sample,
   d. virtually slicing said image, thereby defining, according to the fiducially marked images, N computer-retrievable three-dimensional image slices [3DISs], N is an integer greater than or equal to 2;
   e. preparing a slicing program of suspected computer-retrievable three-dimensional image slices (SISs) from said N 3DISs; and
   f. physically slicing said sample according to said SISs;
   wherein said step of preparing a slicing program comprises a step of defining from said N 3DISs one or more first SISs and one or more second SISs, wherein the slicing plane of said first SISs and the slicing plane of said second SISs are oriented in a non-parallel manner.

2. The method of claim 1, wherein said step of spatially labeling said sample comprises placing said fiducial marker into or onto said sample.

3. The method of claim 1, wherein said step of spatially labeling said sample comprises physically placing an imageable fiducial marker into or onto said sample, biologically placing an imageable fiducial marker into or onto said sample, chemically placing an imageable fiducial marker into or onto said sample, virtually placing a computer-generated fiducial marker into or onto said sample and any combination thereof.

4. The method of claim 1, wherein said step of acquiring images is provided by at least one member of a group consisting CT, MRI, fluorescence and phosphorescence microscopy (FPM), PET, ultrasound, IR and any combination thereof.

5. The method of claim 1, wherein said slicing program is a CAD-based program, a manual program or a combination thereof.

6. The method of claim 1, wherein said step of physically slicing is provided by a device selected from a microtome and vibrotome.

7. A method of guided slicing of histological specimen, comprising:
   a. extracting a sample from an animal;
   b. spatially labeling said sample by a fiducial marker;
   c. acquiring ex vivo, by at least one first imaging device, one or more images of said sample;
   d. virtually slicing said image, thereby defining, according to the fiducially marked images, N computer-retrievable three-dimensional image slices [3DISs], N is an integer greater than or equal to 2;
   e. assigning, by at least one second imaging device, "likelihood" of malignancy for each of said N 3DISs;
   f. defining, from the N 3DISs, M suspected computer-retrievable three-dimensional image slices [SISs], M is an integer greater than or equal to 0;
   g. preparing a slicing program according to said SISs; and
   h. physically slicing said sample according to said SISs;
   wherein said step of preparing a slicing program comprises a step of defining from said N 3DISs one or more first SISs and one or more second SISs, wherein the slicing plane of said first SISs and the slicing plane of said second SISs are oriented in a non-parallel manner.

8. The method of claim 7, wherein said step of spatially labeling said sample comprises placing said fiducial marker into or onto said sample.

9. The method of claim 8, wherein said step of spatially labeling said sample comprises physically placing an imageable fiducial marker into or onto said sample, biologically placing an imageable fiducial marker into or onto said sample, chemically placing an imageable fiducial marker into or onto said sample, and virtually placing a computer-generated fiducial marker into or onto said sample.

10. The method of claim 7, wherein said at least one first and at least one second imaging devices are selected from the group consisting CT, MRI, fluorescence and phosphorescence microscopy (FPM), PET, US, IR and any combination thereof.

11. The method of claim 7, wherein said slicing program is a CAD-based program, a manual program or a combination thereof.

12. The method of claim 7, wherein said step of slicing is provided by a device selected from a microtome and vibrotome.

13. A guided slicing system for histologically obtained specimens, comprising:
   a. a sample kit for extracting a sample from an animal;
   b. a fiducial marker for spatially labeling said sample;
   c. at least one first imaging device for acquiring ex vivo images of said sample in coordination with said fiducial marker;
   d. a processor configured to prepare a slicing program of suspected computer-retrievable three-dimensional image slices (SISs) by virtually slicing said imaged sample to define N computer-retrievable three-dimensional image slices 3DISs, N is an integer greater than or equal to 2; and
   e. either a microtome or a vibrotome to physically slice said sample according to said SISs;
   wherein preparation of said slicing program comprises a step of defining from said N 3DISs one or more first SISs and one or more second SISs, wherein the slicing plane of said first SISs and the slicing plane of said second SISs are oriented in a non-parallel manner.

14. The system of claim 13, wherein said fiducial marker is selected from the group consisting of a physical member, a biological agent, a chemical material and any combination thereof.

15. The system of claim 13, wherein said fiducial marker is a virtual computer-generated marker.

16. The system of claim 13, wherein said at least one first imaging device is selected from the group consisting of CT, MRI, FPM, PET, US, IR and any combination thereof.

17. The system of claim 13, further comprising at least one second imaging device, for assessing "likelihood" of malignancy for each of said N 3DISs.

18. The system of claim 17, wherein said slicing program is a CAD-based program, a manual program or a combination thereof.

* * * * *